United States Patent
Vogt

(10) Patent No.: US 9,622,865 B2
(45) Date of Patent: Apr. 18, 2017

(54) DEVICE AND METHOD FOR THE IN-SITU PRODUCTION OF ARTICULATED SPACERS

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 392 days.

(21) Appl. No.: 14/278,528

(22) Filed: May 15, 2014

(65) Prior Publication Data

US 2014/0343560 A1 Nov. 20, 2014

(30) Foreign Application Priority Data

May 17, 2013 (DE) .......................... 10 2013 209 171

(51) Int. Cl.
*A61F 2/38* (2006.01)
*A61F 2/30* (2006.01)
*B29C 33/42* (2006.01)

(52) U.S. Cl.
CPC ............ *A61F 2/38* (2013.01); *A61F 2/30942* (2013.01); *A61F 2002/30672* (2013.01); *A61F 2002/30677* (2013.01); *A61F 2002/30957* (2013.01); *A61F 2310/00353* (2013.01); *B29C 33/42* (2013.01); *B29C 33/424* (2013.01)

(58) Field of Classification Search
CPC .... B29C 2033/422; B29C 33/424; A61F 2/38
See application file for complete search history.

(56) References Cited

U.S. PATENT DOCUMENTS

2004/0036189 A1 2/2004 Ensign et al.
2010/0292803 A1 11/2010 Giori

OTHER PUBLICATIONS

Canadian Office Action for corresponding Canadian Application No. 2,850,867 dated Jul. 28, 2015.
English Translation of Chinese Office Action dated Oct. 26, 2015 for corresponding Chinese Application No. 201410208921.7.
Australian Office Action for corresponding AU Application No. 2014202498 dated Dec. 23, 2014.
Hovelius et al, "An alternative method for exchange operation of infected arthroplasty", Acta Orthop. Scand. 50: 93-96 (1979).
Younger et al, "The outcome of two-stage arthroplasty using a custom-made interval spacer to treat the infected hip", J. Arthroplasty 12: 615-623 (1997).

(Continued)

*Primary Examiner* — Andrew Yang
(74) *Attorney, Agent, or Firm* — Norris McLaughlin & Marcus, P.A.

(57) ABSTRACT

Devices and methods in-situ produce articular spacers from a bone cement. The devices and methods have a punch surface for forming an articulation surface of a spacer in the bone cement, whereby the bone cement is arranged on a bone surface for fixation of the spacer, whereby the punch surface has a negative image of the articulation surface to be produced, and the surface forming the negative image is open on the side, at least in part, such that the bone cement can be pushed towards the side, away from the articulation surface to be formed. Moreover, the method for producing an articular spacer on a bone may have one or more of the following steps: A) Applying a bone cement to a prepared bone; B) Pressing said device onto the bone cement; and C) Detaching the device from the cured bone cement.

19 Claims, 6 Drawing Sheets

(56) References Cited

OTHER PUBLICATIONS

Figure 1:
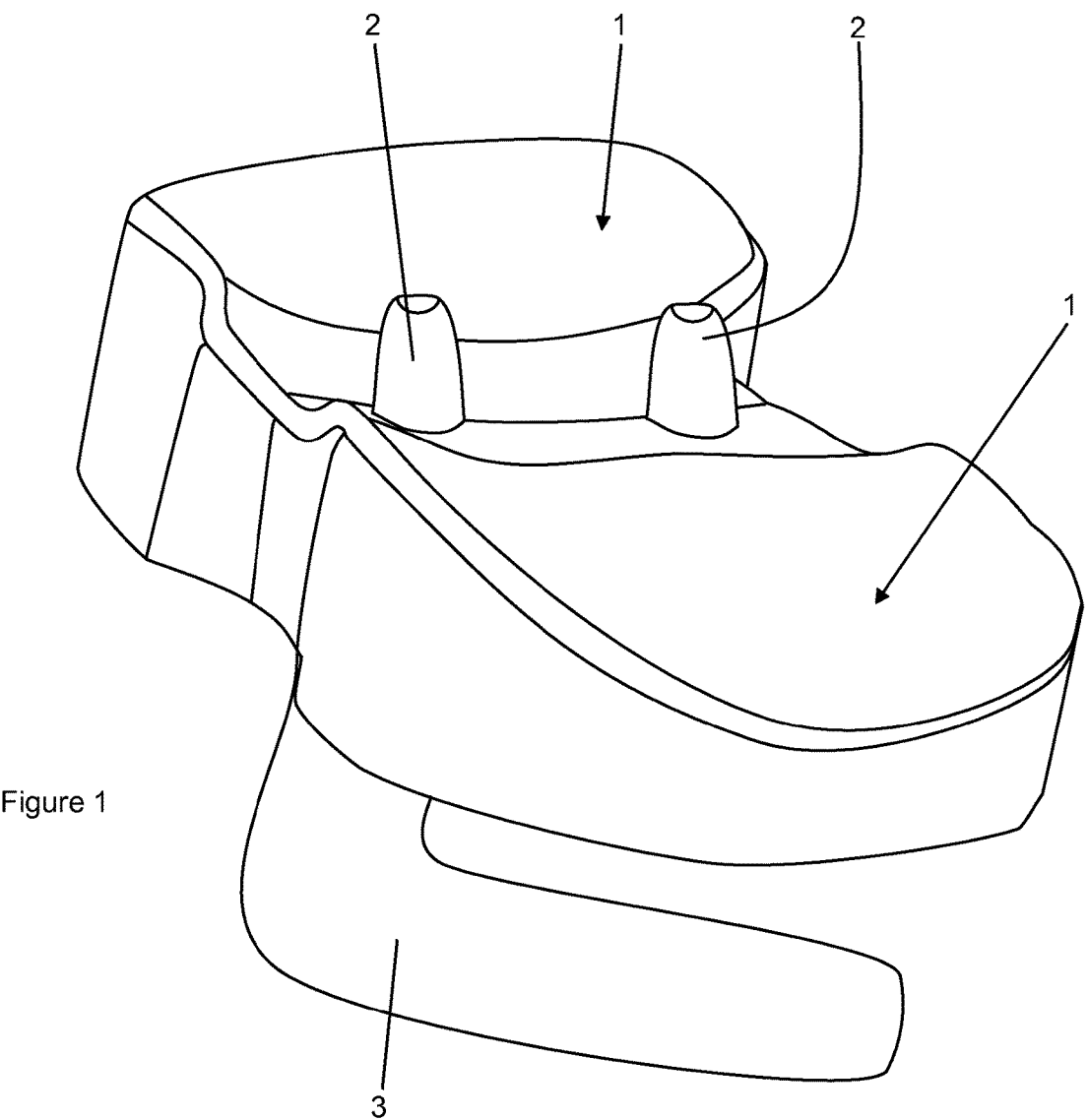

Jones et al, "Salvage of failed total knee arthroplasty: the 'beef-burger' procedure", J. Bone Joint Surg. Br. 71:856-857 (1989).
Cohen et al, "Two-stage reimplantation of septic total knee arthroplasty, Report of three cases using an antibiotic-PMMA spacer block", J. Arthroplasty 3: 369-377 (1988).
McPherson et al, "Techniques in arthroplasty. Use of an articulated PMMA spacer in the infected total knee arthroplasty", J. Arthroplasty 10: 87-89 (1995).
German Office Action in corresponding application DE 10 2013 209 171.0 issued Feb. 4, 2014.

DEVICE AND METHOD FOR THE IN-SITU PRODUCTION OF ARTICULATED SPACERS

The invention relates to a device for the in-situ production of joint spacers from a bone cement, comprising a punch surface for forming an articulation surface of a spacer in the bone cement, whereby the bone cement is arranged on a bone surface for fixation of the spacer, whereby the punch surface comprises a negative image of the articulation surface to be produced. The invention also relates to a set comprising two of said devices, the use of said device, and a method for producing a joint spacer on a bone through the use of said device. The devices are well-suited, in particular, for producing knee spacers.

The knee spacers produced using devices according to the invention are formed in-situ right on the proximal tibia and the distal femur during a surgery using PMMA bone cement dough (polymethylmethacrylate bone cement dough) and the device, without any separate production steps for the knee spacer components and their subsequent anchoring on the proximal tibia and distal femur being needed.

Articular endoprostheses currently have a service life of several years, for example on average more than ten and up to fifteen years in the case of cemented hip endoprostheses. However, undesirable loosening of the articular endoprostheses can occur before the end of the usual service life. This can concern either septic or aseptic loosening. Aseptic loosening means that no microbial germs are detectable yet. There are many causes of aseptic loosening. Aseptic loosening is often related to abrasion at the sliding surfaces of articular endoprostheses. The loosening process in septic loosening is induced by microbial germs. This can either be early or late infections depending on the time of manifestation. Septic loosening is a very serious disease for the patient and associated with high additional costs. It is customary to perform a revision surgery in cases of aseptic and septic loosening alike. This can proceed as a one-stage or a two-stage revision surgery. Two-stage revision surgeries are very common in cases of septic loosening.

In a two-stage revision surgery, the infected articular endoprosthesis is removed in a first surgery followed by debridement and subsequent insertion of a temporary placeholder, a so-called spacer. Said spacer occupies for a number of weeks the space previously occupied by the revised endoprosthesis until the manifest infection has subsided. Said place-holder function is very important in order to effectively prevent muscular atrophy during this period of time and in order to stabilise the existing resection scenario. There are non-articulated and articulated spacers available. Articulated spacers or joint spacers replicate the function of the joint and allow the afflicted limbs to have a certain degree of mobility. This allows the patient to be mobilised early. Articulated spacers are current the state of the art. The spacer is removed in a second surgery, another debridement is done before implanting a cemented or cement-free revision articular endoprosthesis.

The use of spacers is originally based on the work of Hovelius and Josefsson (Hovelius L, Josefsson G (1979), "An alternative method for exchange operation of infected arthroplasty", Acta Orthop. Scand. 50: 93-96). Other early work on spacers includes Younger (Younger A S, Duncan C P, Masri B A, McGraw R W (1997), "The outcome of two-stage arthroplasty using a custom-made interval spacer to treat the infected hip", J. Arthroplasty 12: 615-623), Jones (Jones W A, Wroblewski B M (1989), "Salvage of failed total knee arthroplasty: the 'beefburger' procedure", J. Bone Joint Surg. Br. 71: 856-857), and Cohen (Cohen J C, Hozack W J, Cuckler J M, Booth R E Jr (1988), "Two-stage reimplantation of septic total knee arthroplasty, Report of three cases using an antibiotic-PMMA spacer block", J. Arthroplasty 3: 369-377). McPherson described a concept according to which spacers can be manufactured from bone cement exclusively (McPherson E J, Lewonowski K, Dorr L D (1995), "Techniques in arthroplasty. Use of an articulated PMMA spacer in the infected total knee arthroplasty", J. Arthroplasty 10: 87-89).

Spacers equipped with antibiotics for temporary replacement of knee, hip, and shoulder endoprostheses are available on the market. It is disadvantageous though that the antibiotics contained therein are pre-determined and cannot be adapted specifically to suit the antibiogram of the microbial germs found to be present. In the case of knee spacers, both the tibial component and the femoral component need to be anchored, in addition, to the proximal tibia and the distal femur using polymethylmethacrylate bone cement.

Spacers are often produced by the surgeon using conventional PMMA bone cements and suitable casting moulds. In this context, one or more antibiotic(s) is/are added to the PMMA bone cement powder before spacer production based on the microbial pathogens detected during earlier biopsies and the antibiogram determined. The antibiotics are selected to specifically suit the microbial pathogens present. Said procedure is very advantageous especially if multiple resistant pathogens are present or if a mixed infection by different pathogens is manifest. The spacers produced with casting moulds need to be reworked by mechanical means to remove burs, in particular in the case of hip spacers. In the case of knee spacers, both the tibial and the femoral component of the spacer need to subsequently be fixed to the proximal tibia and the distal femur, respectively, using PMMA bone cement dough. This means considerable time and work are required to produce spacers with casting moulds and implant them subsequently.

In practical application of the two-stage revision surgery of knee endoprostheses, it is therefore also common, after removal of the primary articular endoprosthesis and debridement, to apply PMMA bone cement dough to the proximal tibia and distal femur and to form sliding surfaces in these places by hand.

This interesting concept was pursued further in US 2004/0036189 A1. This reference proposes a casting mould system for knee spacers that is characterised in that the casting moulds for in-situ forming of the spacer components are placed at the proximal tibia and at the distal femur. The proposed elastic casting moulds are filled with PMMA bone cement and then placed right against the bone and are removed after the cement dough has cured. This means that the spacer components are formed, connected to the bone tissue and cured simultaneously in one step. This allows much time and work to be saved. Aside from the contour surface for forming the sliding surfaces, these casting moulds possess a lateral edge that surrounds the contour surfaces and thus forms a space, in which spacer is formed and cured.

However, it is a disadvantage of this casting mould system that the enclosed air does not escape and that air inclusions at the articulation surfaces and/or sliding surfaces of the articular spacers can cause damage and can thus adversely affect the sliding properties of the articulated spacer. Moreover, the casting moulds are difficult to separate from the cured spacer after the PMMA cement dough has cured without damaging or impairing the spacers, and in particular the articulation surfaces and/or sliding surfaces, in the process. Moreover, the casting moulds are complex in structure. Since the casting moulds have to touch against the bone, a large number of different casting moulds need to be kept on hand or even need to be fabricated individually. The application during a surgery could also be simpler and less prone to interference.

Accordingly, it is the object of the invention to overcome the disadvantages of the prior art. In particular, the device and the method should provide an easy way of producing an articulation surface that is as level and smooth as possible and enables the spacer thus generated to be mobile without worsening the mobility of the joint or causing the patient pain due to abrasion at the articulated sliding surfaces of the spacer. The device and the method should be applicable as universally as possible.

It is also an object of the invention to develop a device for the in-situ production of articulated knee spacers which overcomes the disadvantages of previous devices for knee spacer production. The device should enable rapid in-situ forming of the sliding surfaces, whereby the risk of air bubble inclusion should be largely prevented. Moreover, the device should provide for easy detachment off the cured spacer without any damage to the sliding surfaces. The device should be easy and inexpensive to manufacture using technically common plastic materials.

The objects of the invention are met by a device for the in-situ production of articular spacers from a bone cement, comprising a punch surface for forming an articulation surface of a spacer in the bone cement, whereby the bone cement is arranged on a bone surface for fixation of the spacer, whereby the punch surface comprises a negative image of the articulation surface to be produced, and the surface forming the negative image is open on the side, at least in part, such that the bone cement can be pushed towards the side, away from the articulation surface to be formed.

In this context, here and hereinafter, bone surface shall be understood to mean the surface of the bone onto which the bone cement is applied or is being applied for formation of the articular spacer.

The lateral opening allows the inclusion of air to be prevented since the air is pressed out through the lateral openings.

Devices according to the invention can just as well provide the surface representing the negative image to be essentially or over the entire circumference open on the side such that the bone cement can be pushed away laterally in all directions, away from the articulation surface to be formed.

Preferably, at least 70%, particularly preferably at least 90%, particularly preferably the entire circumference, of the surface representing the negative image is open on the side.

In this context, to be open on the side shall be understood to mean that next to the surface representing the negative image there is no adjoining surface that is inclined towards said surface and forms a hollow space between the device and the bone cement to be formed, when the device is pressed onto the bone cement for its intended use.

This is advantageous in that as few as possible, or preferably no, such hollow spaces can be generated between the bone cement and the device during the punching process and/or when the device is pressed against the bone, which would subsequently lead to the formation of hollow spaces in the articulation surface, which would impair the stability of the articulation surface.

The invention can just as well provide at least one separator for placing on the bone to be arranged on the punch surface, in particular on the bone surface, whereby the thickness of the bone cement on the bone surface can be set by means of the separator.

The height of the separator and/or separators relative to the punch surface automatically defines the thickness of the bone cement when the separator is or separators are being pressed onto the bone and/or the bone surface. The thickness of the spacer produced can thus be defined easily. This makes the device very easy to use even in a hectic surgical theatre scenario.

A refinement according to the invention of the invention proposes that at last two separators for placing on the bone are arranged on the punch surface, in particular on the bone surface, by means of which the thickness of the bone cement on the bone surface can be set. The invention can just as well provide three separators for placing on the bone to be arranged on the punch surface in a triangular arrangement with respect to each other.

The separators are an easy means to allow a desired thickness of the bone cement to be applied without air inclusions forming at the articulation surface. Preferably, the separator is or separators are designed to be conically converging in the direction away from the punch surface. It is also preferred to further provide that the separator is or separators are arranged on the inside of the punch surface, rather than on its periphery.

The invention further proposes the height of the separators or separator over the punch surface to be variably adjustable.

This allows various cement dough thicknesses to be produced, meaning that the thickness of the spacer can be produced variably.

According to a preferred refinement, the invention can just as well provide the separator or separators to comprise a bulgable floor for placing on the bone, in particular on the bone surface, whereby the bulgable floor bulges when exposed to a force acting in the direction of the bone, in particular the bone surface, and the punch surface thus becomes detachable from the bone cement formed with the device, whereby the floor preferably is rubber-elastic and the rest of the device is not rubber-elastic.

The device is then particularly simple and easy to detach from the cured cement dough. Due to the bulging of the floor of the separators, the rest of the device lifts off the bone and/or the bone surface.

A preferred refinement of the present invention proposes the device to comprise at least one ejection facility by means of which the punch surface can be mechanically detached from the bone cement formed with the device through the action of a force, whereby the ejection facility is preferably supported as in a bearing in the separator or the ejection facilities are preferably supported as in a bearing in the separators.

This simplifies the detachment of the device from at least largely cured cement dough significantly. Moreover, the defined action of a force can ensure that the spacer thus formed is not exposed to a mechanical strain that might damage the spacer.

In this context, the invention can provide the ejection facility to be an axially mobile pin or pestle or a screw connected to the device by means of a thread by means of which the punch surface side of the device can be pushed away from the bone, in particular from the bone surface, whereby, preferably, the pins, pestles and/or screws of multiple ejection facilities are connected to each other appropriately such that they can be pressed onto the bone, in particular onto the bone surface, only jointly.

Ejection facilities of this type allow easily-dosable and well-directed forces to be exerted on the device in particularly easy manner.

Moreover, the invention can provide in this context that the force of the ejection facility acts on the bone, in particular on the bone surface, perpendicular to the punch surface.

Embodiments having ejection facilities can also provide the ejection facility to be arranged in an opening perpendicular to the punch surface or the ejection facilities to be arranged in openings perpendicular to the punch surface.

These measures prevent torsional forces and torques, which might damage the spacer upon detachment of the device.

A refinement of the invention proposes at least one handle for pressing the device against the bone to be arranged on the side facing away from the punch surface and/or on the lateral surface of the device adjacent to the punch surface.

This simplifies the operation of the device and helps, in particular, with the use of the ejection facility.

For build-up of devices according to the invention, the invention can provide that the device is essentially made of a thermoplastic material, preferably of polypropylene, polyethylene, polytetrafluoroethylene, polyethyleneterephthalate, polybutyleneterephthalate, Polyamide-6, Polyamide-6.6, Polyamide-10, Polyamide-12 or mixtures thereof, whereby the device preferably consists of the afore-mentioned materials except for the bulgable floor, pins, pestles and/or screws.

These materials are inexpensive and well-suited for the manufacture of the devices. Moreover, they can be disinfected well and are thus particularly well-suited for building-up punches in the medical field.

The invention can just as well provide the device to be a punch, preferably a tibia punch for forming a tibial plateau and/or a femur punch for forming a condylar surface.

In this context, the invention can provide the ejection facilities of the tibia punch to be arranged to be asymmetrical to a plane in the knee that is parallel to the sagittal plane of the patient and/or the ejection facility or the ejection facilities of the femur punch to be arranged between the moulds for the condyles to be formed, preferably to be oriented such as to be axial to the femur axis.

The objects of the invention are also met by a set comprising two devices according to any one of the preceding claims, whereby the first device is intended for forming the articulation surface of a first articular spacer and the second device is intended for forming the articulation surface of a second articular spacer, whereby the two articulation surfaces touch against each other and form the sliding surfaces of the articular spacer in the patient-inserted state such that the articular spacer assumes the function of the bones of the respective joint, preferably of a knee joint.

The set is advantageous in that the devices of the set already possess matching punch shapes such that the articulation surfaces of the spacers and/or spacer parts generated match each other.

The objects of the invention are also met by the use of said device or said set for in-situ forming at least one articular spacer, preferably for in-situ forming a tibial spacer and/or a femoral spacer.

The underlying objects of the invention are also met by a method for producing an articular spacer on a bone, in particular the bone surface, comprising the following chronological procedural steps:

A) Applying a bone cement to a prepared bone;

B) Pressing a device according to the invention onto the bone cement; and

C) Detaching the device from the cured bone cement.

The bone cement need not be fully cured in step C), but must no longer have a doughy consistency. Regardless, it is preferred according to the invention for the bone cement to be fully cured for detachment of the device.

In this context, the invention can provide the bone cement to cure after step A) and before step B) to the point at which it assumes a doughy consistency. A doughy consistency is attained once the bone cement is sufficiently viscous such that it can still be shaped without the surface tension of the bone cement leading to a deformation of the surface of the bone cement.

Moreover, according to the invention it can be preferred to provide that the device in step C) is detached from the formed bone cement surface through the use of the ejection facility, preferably by means of rotating at least one screw as ejection facility and/or by pressing onto at least one pin or at least one pestle as ejection facility and/or through bulging the floor of the separators, in particular by means of at least one pin or at least one pestle or at least one screw as ejection facility.

The invention also proposes that the device is pressed appropriately onto the bone cement in step B) such that the separator or separators rests or rest on the bone, in particular on the bone surface.

Finally, the invention can provide that excessive bone cement protruding on the side beyond the articulation surface is removed after step C).

The invention is based on the surprising finding that the presence of open lateral surfaces allows a punch to be provided that has no or only few hollow space-generating side walls such that no or hardly any air inclusions can be produced on the articulation surface of the spacer to be produced, since the air inclusions are pressed out on the side together with the excessive cement. As a result, the articulating surface of the spacer thus produced becomes smoother and the risk of particles detaching from the surface of the sliding surface and then leading to complications is reduced.

The invention is also based on the insight that a doughy (viscous) bone cement can be formed without any trouble without a fully enclosing casting mould provided it is not too fluid. The suitable doughy consistency can be attained by waiting a certain period of time after application of the bone cement onto the bone until the cement starts to cure, and/or starts to become more viscous, or by providing a bone cement mixture of the desired consistency in the first place. A device of this type, which is not bordered on its sides or only in part, does not have to touch against the bone with its circumference such that the device can be used variably for many different patients and/or different bone geometries.

The underlying rationale of the invention is to use punches to form the articulation surfaces and/or sliding surfaces, whereby the punches preferably contain at least one mobile ejector by means of which the punches can be detached from the cured PMMA cement. This means that the medical user brushes a PMMA cement that is modified with suitable antibiotics, for example, onto the proximal tibia and/or the distal femur. Then, the tibial articulation surface and/or sliding surface is formed by pressing a tibia punch onto the bone cement. The thickness of the tibial spacer is pre-determined by the distance of the contact surface of the ejector to the contour of the punch. The punch can be removed either when the PMMA cement dough is no longer flowable or when the PMMA cement is already fully cured. The femur punch works likewise, whereby the articulation surfaces and/or sliding surfaces of the condyles are formed by the femur punch. The subsequent procedure is analogous to the one illustrated above for the tibia punch.

It is essential that the device, i.e, for example, the tibia punch or the femur punch, does not comprise an edge, which, together with the contour surface, might form a hollow space. This enables excessive PMMA cement to escape on the edges and air inclusions to easily exit from the cement dough. This prevents air inclusion-induced defects in the articulation surfaces and/or sliding surfaces to be prevented effectively. The excessive cement dough can be removed at the same time or afterwards without any difficulty by hand or with spatulas. It is crucial that the articulation surfaces thus produced are smooth and free of defects.

An inventive device for producing knee joint spacers using PMMA bone cements is characterised, for example, in that the device consists of two components A and B, whereby component A consists of a) a tibia punch (first device) whose underside has a negative contour with respect to the tibial plateau (articulation surface of the tibia) to be formed;

b) whereby the punch comprises at least one continuous opening perpendicular to the contour;

c) whereby at least one shiftable ejector (ejection facility) is provided that can be shifted perpendicular to the contour through the at least one opening of the punch;

d) whereby the punch comprises at least one handle on its upper side; and e) whereby the tibia punch does not possess any side walls bordering the contour-forming surface that might form a hollow space;

and component B consists of a) a femur punch (second device) whose underside has a negative contour with respect to the condyles (articulation surface of the femur) to be formed;

b) whereby the punch comprises at least one continuous opening perpendicular to the contour;

c) whereby at least one shiftable ejector (ejection facility) is provided that can be shifted perpendicular to the contour through the at least one opening of the punch;

d) whereby the femur punch comprises at least one handle on its upper side; and e) whereby the femur punch does not possess any side walls bordering the contour-forming surface that might form a hollow space.

The invention can also provide the at least one ejector of the tibia punch and/or femur punch to be movable perpendicular to the forming contour by shifting it linearly by hand or by screw motions.

Moreover, the invention can provide that the at least one ejector possesses at least one contact surface that rests on the tibial/femoral bone, whereby the contact surface of the ejectors preferably is rubber-elastic.

A preferred and advantageous refinement consists of the ejector being graduated and of the distance between the contact surface of the ejector and the contour of the tibia punch/femur punch being definable.

According to the invention, the tibia punch/femur punch is made from a material that is not rubber-elastic, except for the contact surface of the ejector.

Component A according to the invention is used for the in-situ forming of tibial spacers and component B according to the invention is used for the in-situ forming of femoral spacers.

Figure 2:
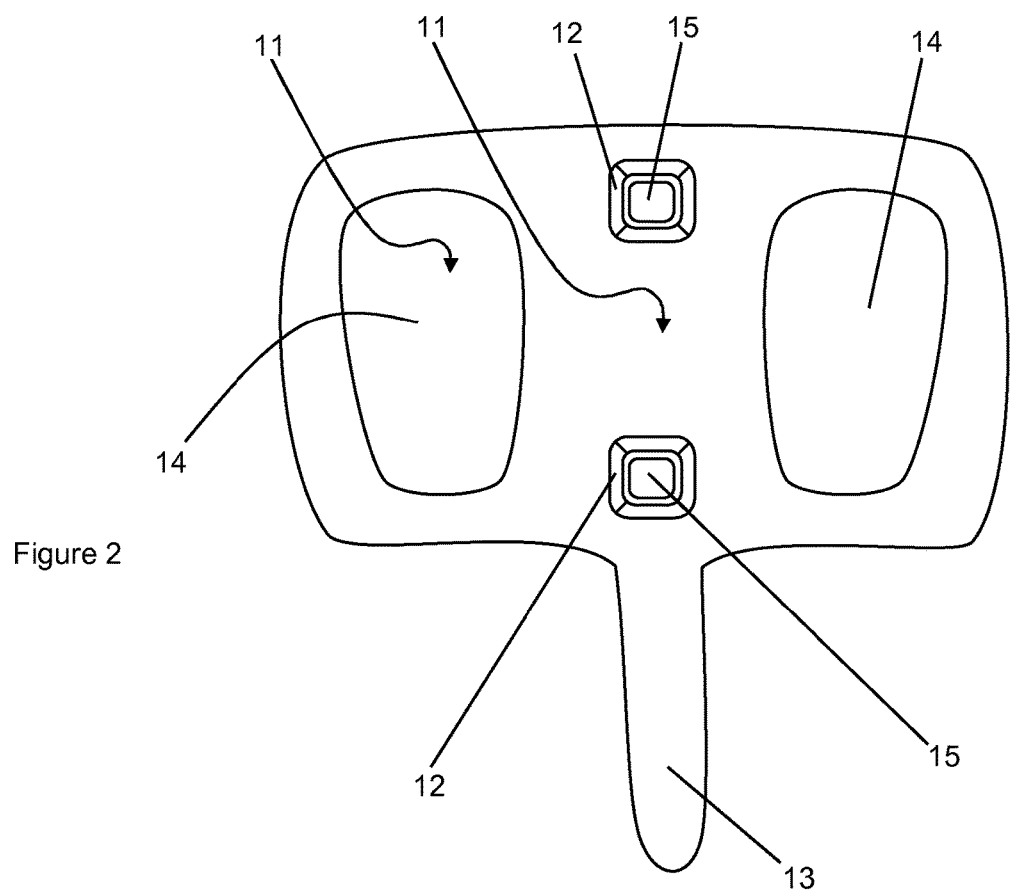
Figure 3:
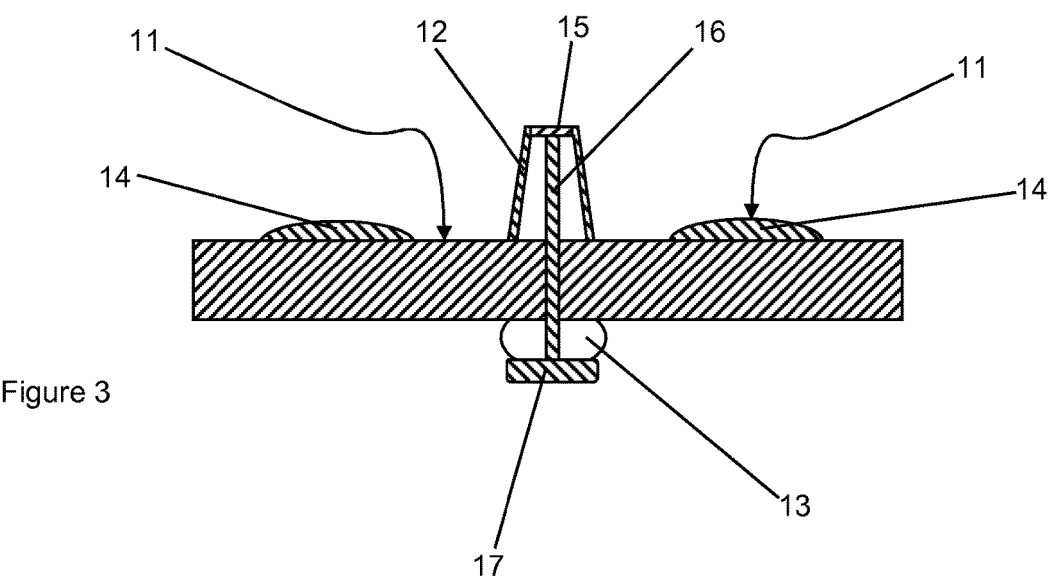
Figure 4:
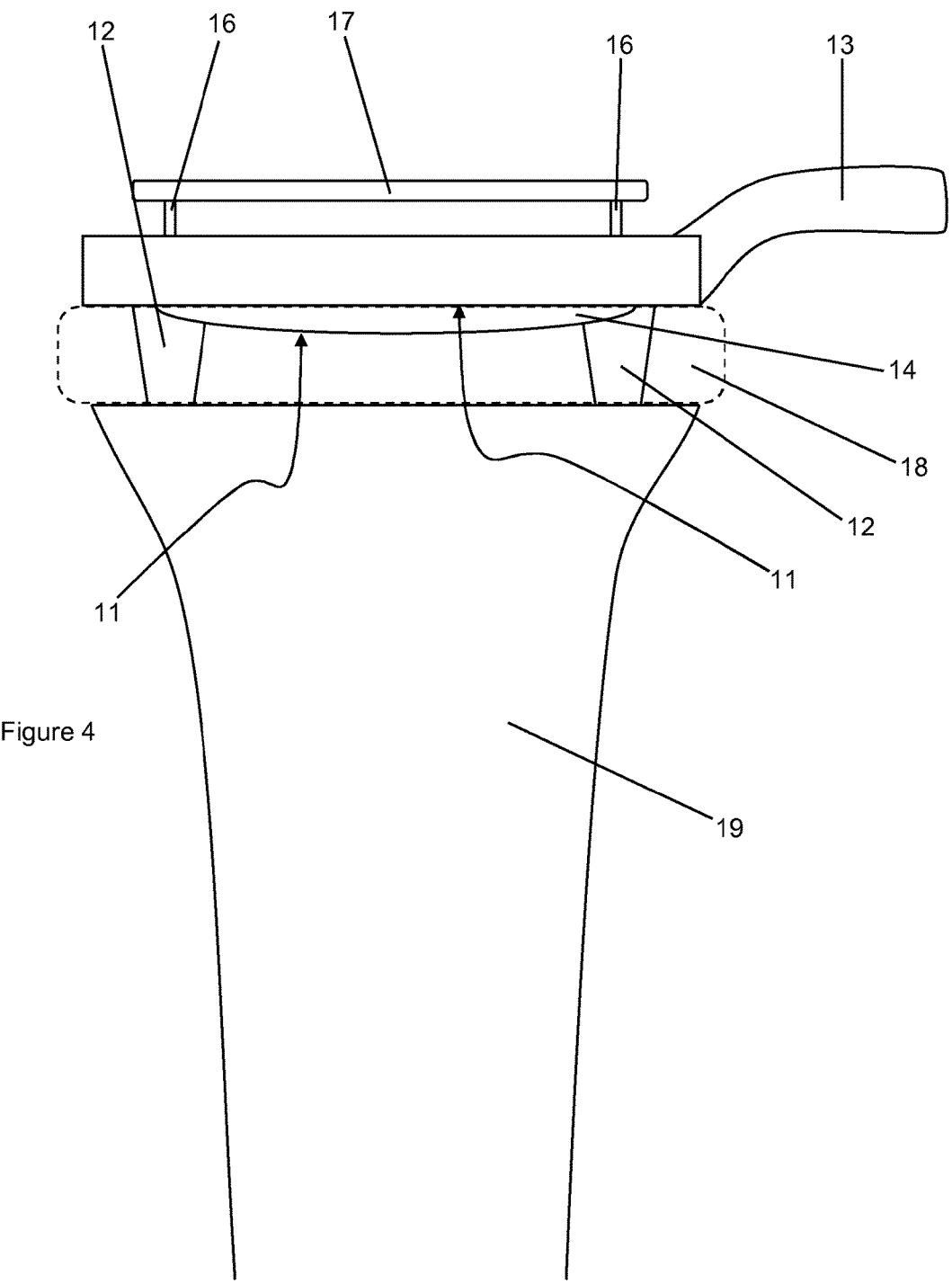
Figure 5:
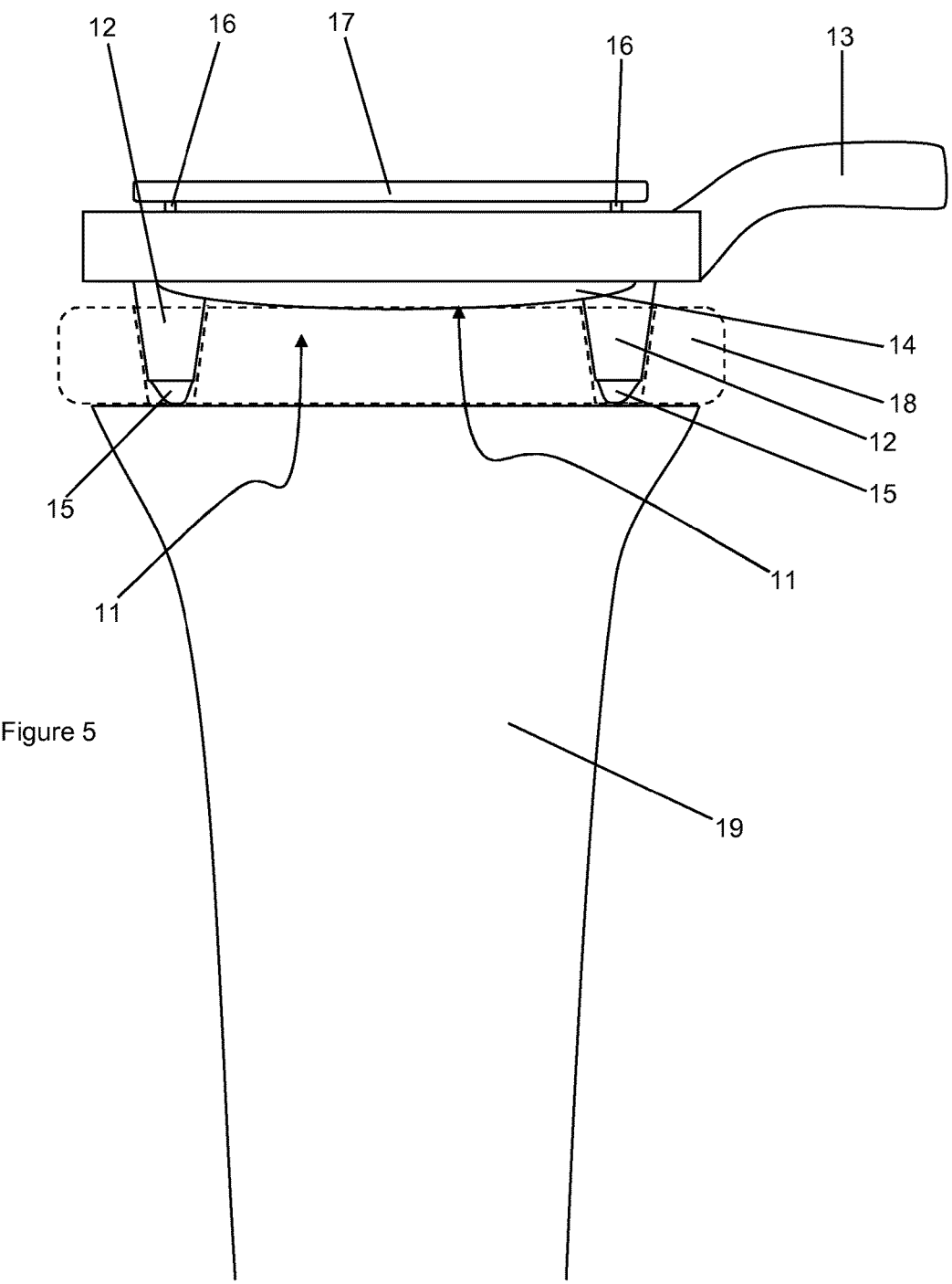
Figure 6:
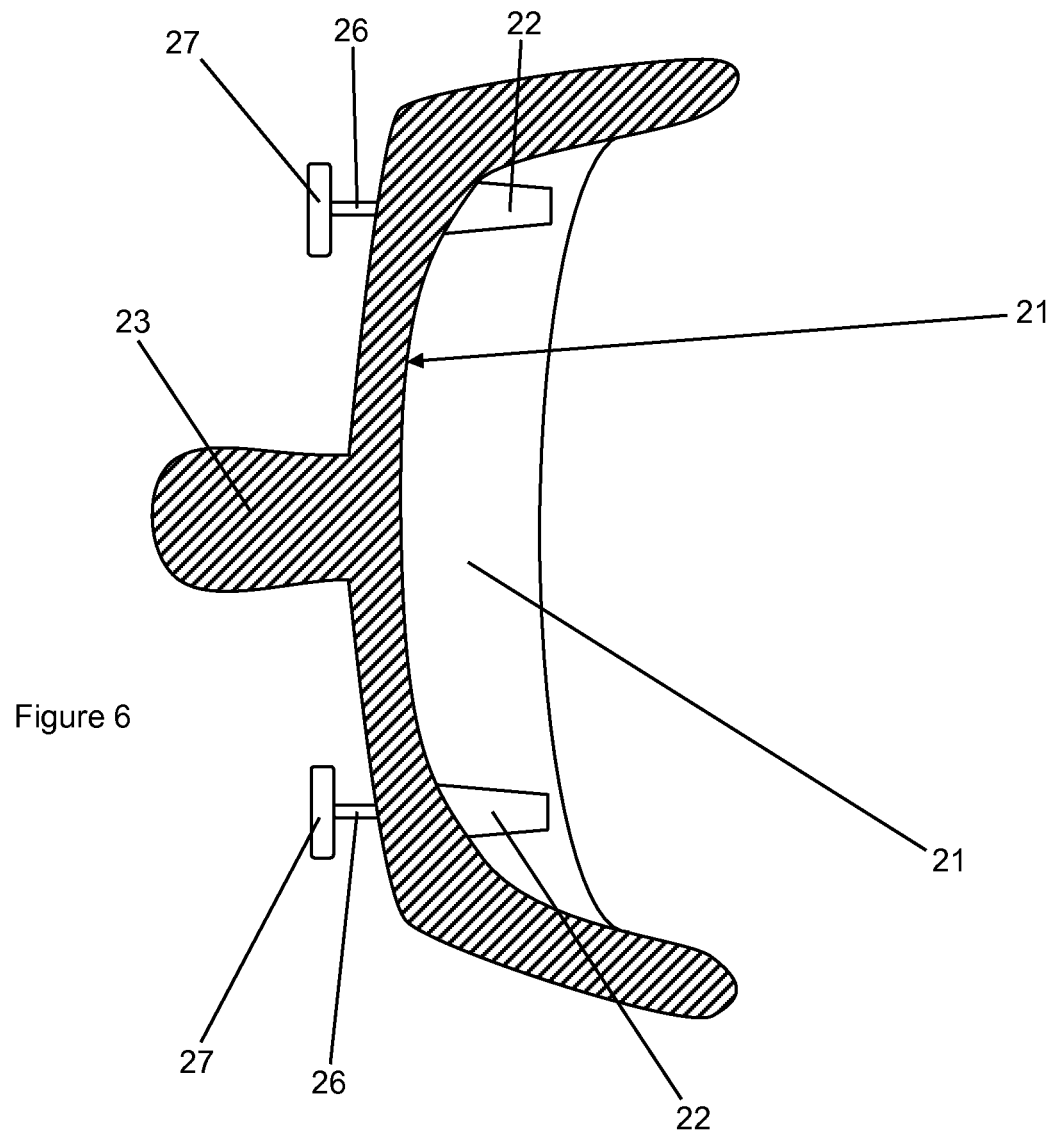

Exemplary embodiments of the invention shall be illustrated in the following on the basis of six schematic figures, though without limiting the scope of the invention. In the figures:

FIG. 1: shows a schematic perspective view of a femur punch according to the invention;

FIG. 2: shows a schematic top view onto a tibia punch according to the invention;

FIG. 3: shows a schematic cross-sectional view through the tibia punch according to FIG. 2;

FIGS. 4 and 5: show a schematic side view of the tibia punch according to FIGS. 2 and 3 in an application scenario; and FIG. 6: shows a schematic cross-sectional view of a femur punch according to the invention.

FIG. 1 shows a schematic perspective view of a femur punch according to the invention made from a thermoplastic material. In the view shown in FIG. 1, the femur punch comprises a punch surface 1 facing upwards that is intended for forming an articulation surface in a bone cement (not shown), whereby the bone cement is arranged on a prepared end of a femur. For this purpose, the bone cement adheres to the contact surface on the femoral bone. When the starting components of the bone cement react with each other, the bone cements first gets doughy, i.e. more viscous. In this condition, the punch surface 1 of the femur punch is pressed onto the bone cement. The fully cured bone cement later forms a femur joint spacer and replicates at least the condyles of the femur.

The thickness of the bone cement and thus of the spacer later on is determined by the height of two separators 2 that are arranged on a central plane of the femur punch. The flattened ends of the separators 2 serve as contact surfaces on the femoral bone in the region onto which the bone cement is applied also. In this central plane, the punch surface 1 is curved slightly inwards. The two outer regions of the punch surface 1 that are curved inwards are to form the sliding surfaces of the condyles of the spacer in the bone cement.

When the femur punch is pressed onto the bone cement, the bone cement can flow off on all sides beyond the punch surface 1, since the femur punch has no side walls that would protrude beyond the edges of the punch surface 1. This can ensure that the articulation surface or sliding surface of the spacer produced from the bone cement produced through the punch surface 1 is smooth and comprises no holes caused by air inclusions between the punch surface 1 and the bone cement.

A handle 3 is provided on the side of the femur punch opposite from the punch surface 1 and can be used to hold and operate the femur punch by hand.

FIGS. 2 and 3 show a schematic top view onto a punch surface 11 of a tibia punch according to the invention, which essentially consists of a hard plastic material such as, for example, polypropylene, polyethylene and/or a polyamide. FIG. 3 shows a schematic cross-sectional view through the tibia punch according to FIG. 2.

Two conical separators 12 are arranged in the middle of the punch surface and are elevated over the punch surface 11. A handle 13, by means of which the tibia punch can be pressed onto a bone cement, is arranged on one side of the tibia punch along a central axis of the tibia punch that connects the centres of the two separators 12.

The punch surface 11 is structured to have two running surface moulds 14 which are elevated from the plane of the punch surface 11 (in the direction of the observer in FIG. 2).

The planar floor surfaces 15 of the separators 12 serving as contact surfaces on the bone are made, in their centre, of a rubber-elastic or a suitably pre-tensioned material. This allows the floor surfaces 15 to be made to bulge in the direction of the bone.

Pins 16 and/or pestles 16 are arranged inside the separators and are supported as in bearings along their central axis in openings in the tibia punch such as to be mobile. The pins 16 and/or pestles 16 project beyond the side of the tibia punch that is opposite to the punch surface 11. In this location, they are connected to an actuation strip 17 that rigidly connects the two pins 16 and/or pestles 16 to each other. Pressing on the actuation strip 17 causes the pins 16 and/or pestles 16 to press onto the inside of the floor surfaces 15 and to make these bulge outwards.

FIG. 4 shows a schematic side view of the tibia punch according to FIGS. 2 and 3 in an application scenario. The tibia punch is shown to be pressed onto a bone cement 18 and onto an end of a tibial bone 19. In order to illustrate the arrangement of the separators 12 and of the punch surface 11, the bone cement 18 is shown as if it was transparent in FIG. 18 and is therefore indicated as a rectangular shape with rounded corners just by a dashed line.

The running surface moulds 14 are to form the inwards-curving tibial sliding surfaces of the spacer in a bone cement 18. The tibial sliding surfaces can then slide, for example, against the sliding surfaces of the condyles of a spacer formed using a device according to FIG. 1 or 5, and thus replicate the function of a knee joint. The thickness of the bone cement 18 is determined by the separators 12 that have been placed on the bone 19.

When the tibia punch is pressed onto the viscous (doughy) bone cement 18, as shown in FIG. 4, the punch surface 11 forms the surface of the bone cement 18. Simultaneously, any excess of bone cement 18 is pressed away towards the sides without air inclusions forming between the punch surface 11 and the bone cement. After the bone cement 18 is cured, the actuation strip 17 is actuated by pressing it in the direction of the tibial bone 19. The pressure exerted by the pins 16 and/or pestles 16 then cause the rubber-elastic floor surfaces 15 to bulge in the direction of the bone 19 and thus deforms the floor surfaces 15. The floor surfaces 15 are made to bulge and the tibia punch lifts of the cured or at least no longer flowable bone cement 18. This situation is shown in FIG. 5.

Basically, it is also feasible to provide floor-side feedthroughs through the separators instead of a rubber-elastic floor 15 such that the tips of the pins 16 and/or pestles 16 rest directly on the bone 19 and to lift the tibia punch off the bone cement 18 by this means. However, the feedthroughs need to fit well with the pins 16 and/or pestles 16 for this purpose such that the bone cement 18 can not or hardly flow into the intervening spaces where it cures and renders any motion of the pins 16 and/or pestles 16 with respect to the separators 12 and the entire rest of the punch impossible.

The invention can just as well provide that a major part of the separators 12 or the entire separators 12 are made from a rubber-elastic material. The deformation then allows the separators 12 also to detach better from the bone cement. However, this may result in some inaccuracy in the thickness of the spacer thus produced.

The function of the pins 16 and/or pestles 16 and of the separators 12 discussed here can be translated easily and within the scope of the invention to femur punches or other devices according to the invention.

FIG. 6 shows a schematic cross-sectional view of a femur punch according to the invention. The femur punch has a punch surface 21 for forming a sliding surface in a bone cement. For this purpose, the femur punch forms the condylar surfaces of the bone cement spacer in-situ, during a surgery, on a femur.

The thickness of the bone cement spacer thus produced is determined by two separators 22. A handle 23 is arranged on the side of the femur punch opposite from the punch surface 21 and can be used to press the femur punch onto a bone cement.

Two screws 26 having screw heads 27 are supported as in bearings in matching internal threads such that they can be screwed in the direction of the screw axes and are mobile with respect to the rest of the femur punch. The screws 26, much like the pins 16 and/or pestles 16 according to FIGS. 2 to 5, serve for deformation of the floors of the separators 22 and thus for detaching the femur punch from the cured bone cement spacer. The pins 16 and/or pestles 16 and the screws 26 are advantageous in that they allow the punches to be detached from the cured or no longer flowable bone cement without any need for torsional forces or torques having unfavourable effects. However, if the punches are lifted off with little care using the handles 3, 13, 23, for example by leverage, the articulation surfaces just produced might be damaged.

The features of the invention disclosed in the preceding description and in the claims, figures, and exemplary embodiments, can be essential for the implementation of the various embodiments of the invention both alone and in any combination.

LIST OF REFERENCE NUMBERS 1, 11, 21 Punch surface
2, 12, 22 Separator
3, 13, 23 Handle
14 Running surface mould
15 Rubber-elastic floor
16 Pin
17 Actuation strip
18 Bone cement
19 Bone
26 Screw
27 Screw head

The invention claimed is:

1. A device for in-situ production of articular spacers from a bone cement, the device comprising a punch surface for forming an articulation surface of a spacer in the bone cement, wherein the bone cement is arrangeable on a bone surface for fixation of the spacer, wherein the punch surface comprises a negative image of the articulation surface to be produced, and the surface forming the negative image is open on a side, at least in part, such that the bone cement is pushable towards a side, away from the articulation surface to be formed, wherein at least one separator for placing on a bone is arranged on the punch surface, wherein a thickness of the bone cement is settable by means of the at least one separator.

2. The device according to claim 1, wherein the surface representing the negative image is at least partially over the entire circumference open on the side such that the bone cement is pushable laterally in all directions.

3. The device according to claim 1, wherein at least two separators for placing on a bone are arranged on the punch surface by means of which a thickness of the bone cement is settable.

4. The device according to claim 3, wherein a height of the at least two separators or the at least one separator above the punch surface can be set variably.

5. The device according to claim 3, wherein the at least one separator or the at least two separators comprise(s) a bulgable floor for placing on the bone or on the bone surface, wherein the bulgable floor bulges when exposed to a force acting in the direction of the bone, and the punch surface thus becomes detachable from the bone cement formed with the device, wherein the floor is rubber-elastic and the rest of the device is not rubber-elastic.

6. The device according to claim 1, further comprising at least one ejection facility by means of which the punch surface is mechanically detachable from the bone cement formed with the device through the action of a force, wherein the ejection facility is supported as in a bearing in the separator or ejection facilities are supported as in a bearing in the separators.

7. The device according to claim 6, wherein the ejection facility is an axially mobile pin or pestle or a screw connected to the device by means of a thread by means of which the punch surface side of the device is pushable away from the bone or from the bone surface, wherein the pins, pestles and/or screws of multiple ejection facilities are connected to each other appropriately such that the pins, pestles and/or screws are pressable onto the bone or onto the bone surface, jointly.

8. The device according to claim 6, wherein force of the ejection facility is adapted to act on the bone or on the bone surface, perpendicular to the punch surface.

9. The device according to claim 6, wherein the ejection facility is arranged in an opening perpendicular to the punch surface or in that the ejection facilities are arranged in openings perpendicular to the punch surface.

10. The device according to claim 1, wherein at least one handle for pressing the device onto the bone is arranged on the side facing away from the punch surface and/or on the lateral surface of the device adjacent to the punch surface.

11. The device according to claim 1, wherein the device is made of a thermoplastic material comprising polypropylene, polyethylene, polytetrafluoroethylene, polyethyleneterephthalate, polybutyleneterephthalate, Polyamide-6, Polyamide-6.6, Polyamide-10, Polyamide-12 or mixtures thereof, wherein the device consists of the thermoplastic material except for bulgable floor, pins pestles and/or screws.

12. The device according to claim 6, wherein the device is a tibia punch for forming a tibial plateau and/or a femur punch for forming a condylar surface.

13. The device according to claim 12, wherein the ejection facilities of the tibia punch are arranged to be asymmetrical to a plane in a knee that is parallel to a sagittal plane of a patient and/or the ejection facility or the ejection facilities of the femur punch are arranged between moulds for condyles to be formed and are oriented such as to be axial to the femur axis.

14. A set comprising at least a pair of the devices according to claim 1, wherein a first device according to claim 1 is adapted for forming the articulation surface of a first articular spacer and a second device according to claim 1 is adapted for forming the articulation surface of a second articular spacer, wherein the two articulation surfaces touch against each other and form the sliding surfaces of the articular spacer in the patient-inserted state such that the articular spacer assumes a function of the bones of the respective joint.

15. A method for producing an articular spacer on a bone or a bone surface, the method comprising:
A) applying a bone cement to a prepared bone or bone surface;
B) pressing the device according to claim 1 onto the bone cement; and
C) detaching the device from the bone cement after the bone cement at least partially cures.

16. The method according to claim 15, wherein the bone cement cures after step A) and before step B) to the point at which the bone cement has a doughy consistency.

17. The method according to claim 15, wherein the device, in step C), is detached from the formed bone cement surface through use of at least one ejection facility, by means of rotating at least one screw as the at least one ejection facility, and/or by pressing onto at least one pin or at least one pestle as the at least one ejection facility and/or through bulging the floor of the at least one separator, by means of the at least one pin or the at least one pestle or the at least one screw as the at least one ejection facility.

18. The method according to claim 17, wherein the device, in step C), is detached from the formed bone cement surface by means of rotating the at least one screw as the at least one ejection facility and/or by pressing onto the at least one pin or the at least one pestle as the at least one ejection facility and/or through bulging the floor of the at least one separator, by means of the at least one pin or the at least one pestle or the at least one screw as the at least one ejection facility.

19. The method according to claim 15, wherein the device is pressable onto the bone cement in step B) such that the at least one separator rests on the bone or on the bone surface.

* * * * *